United States Patent
Sliwa et al.

(10) Patent No.: US 8,628,473 B2
(45) Date of Patent: Jan. 14, 2014

(54) ACOUSTIC TRANSDUCER FOR PULSE-ECHO MONITORING AND CONTROL OF THERMALLY ABLATIVE LESIONING IN LAYERED AND NONLAYERED TISSUES, CATHETER CONTACT MONITORING, TISSUE THICKNESS MEASUREMENT AND PRE-POP WARNING

(75) Inventors: John Sliwa, Los Altos Hills, CA (US); Zhenyi Ma, San Jose, CA (US); Stephen Morse, Menlo Park, CA (US)

(73) Assignee: St. Jude Medical, Inc., St. Paul, MN (US)

(*) Notice: Subject to any disclaimer, the term of this patent is extended or adjusted under 35 U.S.C. 154(b) by 201 days.

(21) Appl. No.: 13/085,867

(22) Filed: Apr. 13, 2011

(65) Prior Publication Data
US 2012/0265069 A1     Oct. 18, 2012

(51) Int. Cl.
  *A61B 8/00* (2006.01)
(52) U.S. Cl.
  USPC ........................... 600/439; 606/28
(58) Field of Classification Search
  USPC ........................... 600/439; 606/28
  See application file for complete search history.

(56) References Cited

U.S. PATENT DOCUMENTS

| | | | |
|---|---|---|---|
| 5,747,672 A * | 5/1998 | Parent et al. | 73/61.79 |
| 5,846,205 A | 12/1998 | Curley et al. | |
| 6,406,433 B1 | 6/2002 | Mamayek | |
| 6,416,492 B1 | 7/2002 | Nielson | |
| 7,666,143 B2 | 2/2010 | Wilser et al. | |
| 7,678,056 B2 | 3/2010 | Wilser et al. | |
| 7,976,537 B2 | 7/2011 | Lieber et al. | |
| 2003/0130657 A1 * | 7/2003 | Tom et al. | 606/47 |
| 2006/0142672 A1 | 6/2006 | Keast et al. | |
| 2006/0264757 A1 | 11/2006 | Maschke | |
| 2008/0071173 A1 * | 3/2008 | Aldrich | 600/439 |
| 2008/0119694 A1 | 5/2008 | Lee | |
| 2008/0287810 A1 * | 11/2008 | Park et al. | 600/478 |
| 2010/0144904 A1 | 6/2010 | Wang et al. | |

OTHER PUBLICATIONS

S.G. Demos, et al., "Real time assessment of RF cardiac tissue ablation with optical spectroscopy", Optics Express, Sep. 12, 2008, 11 pp., vol. 16, No. 19, Optical Society of America, CA, USA.

* cited by examiner

*Primary Examiner* — Jonathan Cwern
(74) *Attorney, Agent, or Firm* — Mattingly & Malur, P.C.

(57) ABSTRACT

An ablation catheter with acoustic monitoring comprises an elongated catheter body; a distal member disposed adjacent a distal end and including an ablation element to ablate a biological member at a target region outside the catheter body; and one or more acoustic transducers each configured to direct an acoustic beam toward a respective target ablation region and receive reflection echoes therefrom. The distal member includes a transducer housing in which the acoustic transducers are disposed, the transducer housing including at least one transducer window which is the only portion in the distal member through which the acoustic beam passes, at least the at least one transducer window portion of the distal member being made of a material comprising at least 50% carbon by volume, the transducer window material having an acoustic impedance between that of the acoustic transducers and that of the biological member.

25 Claims, 6 Drawing Sheets

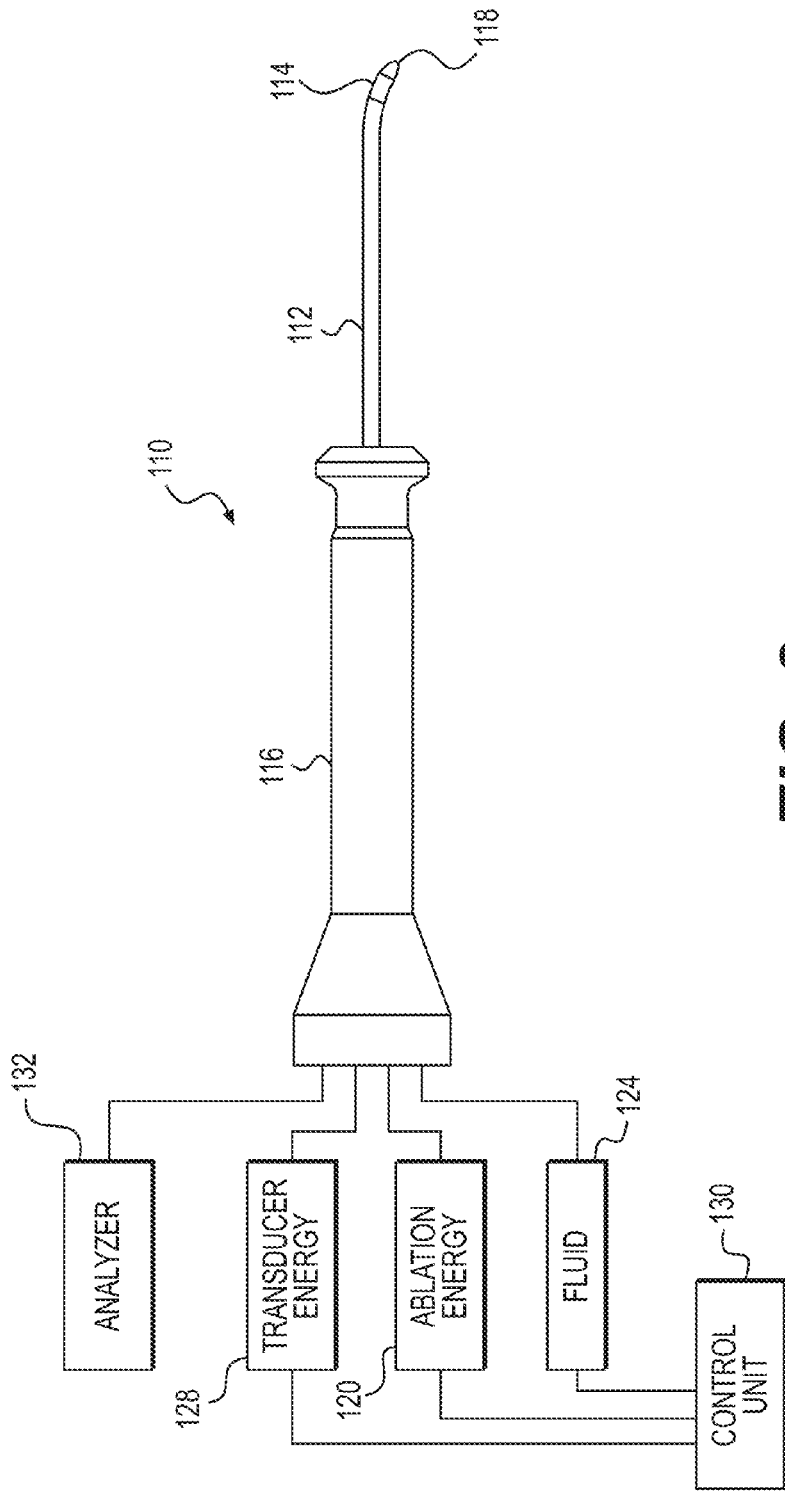

ACOUSTIC TRANSDUCER FOR PULSE-ECHO MONITORING AND CONTROL OF THERMALLY ABLATIVE LESIONING IN LAYERED AND NONLAYERED TISSUES, CATHETER CONTACT MONITORING, TISSUE THICKNESS MEASUREMENT AND PRE-POP WARNING

BACKGROUND OF THE INVENTION

The present invention relates generally to acoustic transducers and, more specifically, to acoustic transducers for lesion feedback, catheter tip contact-monitoring, tissue thickness measurement, and pre-pop warning.

Cardiac ablation practitioners would like lesion feedback and contact monitoring from their thermal (e.g., radiofrequency or RF) ablation catheters. They would preferably also like to further know the thickness of target tissues and the proximity of organs to be avoided such as the esophagus, aorta, and lungs. Finally, some warning of pre-pop conditions would also be quite valuable. By "contact" we mean at least verification of intimate tissue contact of the ablating catheter tip, and even more preferably, also the measurement of the actual contact force involved. The contact force is of interest in order to avoid unintended tissue puncture and to guarantee good ablative results.

Electrically based RF ablation catheter lesion-feedback products now in development use indirect approaches comprising monitoring of electrical tip-coupling RF-impedances or parameters based on such tissue-coupling impedances measured at various RF frequencies including frequencies different than the RF ablation frequency. They essentially take advantage of the already existing electrical coupling of the tip to tissue to electrically deduce information about the lesion size. These are indirect approaches offering some additional value over simply monitoring the impedance only at the RF ablation frequency which as has long been the practice.

Proposed optical methods for lesion feedback include those disclosed by Biosense-Webster wherein the total integrated optical back-scattering of ablating tissue is monitored. In this approach, illumination light is directed into target tissues from a juxtaposed RF ablating catheter tip and, as lesioning proceeds, light is increasingly back-scattered from various depths of the forming lesion volume giving an indirect but still useful indication of total lesion volume based on total integrated back-scatter. One potential disadvantage of optical techniques, other than the cost for a multi-fiber fiber-optic solution, is that tissue surface charring can partially blind the probe by blocking all light penetration at the tissue surface. As such, this must be avoided and/or accounted for.

Determination of catheter ablator tip tissue-contact has long been done by (a) monitoring the electrical contact impedance at the RF ablation frequency, and possibly also (b) monitoring the apparent deformed shape of the catheter in an X-ray fluoroscopy image in addition to (a). More recently, a number of optical methods utilizing optical fibers have been suggested and are being developed such as that of Enclosense Inc. wherein optical fibers are used to monitor tip displacements and therefore tip forces. Approaches which utilize 3 or more such optical fibers plus dedicated LEDS and photodiodes can become expensive to manufacture and do not leave much room for other important catheter components such as catheter steering wires and fluid lumens. They also will have a somewhat higher failure rate, higher manufacturing cost, and lower manufacturing yield given the large number of added components. However they can work.

We utilize one or more pinging acoustic transducers mounted in or adjacent the catheter tip to acoustically detect lesion volume and tissue-contact if not also tissue contact force. Unlike the above optical backscatter approach, the acoustic pulse-echo approach also allows a user to discern the lesion state at specific depths because time-delay range data is available. This also allows for direct measurement of tissue thickness or organ proximity.

One might ask why not instead simply utilize ICE probes (intracardiac echo ultrasonic phased-array imaging probes) to image all of the ablation catheter, the lesion(s), and the heart chamber(s). There are several reasons for this including the following. (a) It is a separate additional fairly expensive device. (b) Currently available ICE imaging catheters image 2D slices. It is not easy in a beating heart to find and remain aimed at the ablating catheter tip given that the 2D ICE image plane must be aligned perfectly with the ablating tip. (c) During ablation the lesion is under the ablating catheter tip and you cannot see through the tip from the blood pool. ICE imaging catheters are still eagerly employed by many practitioners today for general visualization of target anatomy but they do not yet provide useful lesion information for the above and additional reasons.

BRIEF SUMMARY OF THE INVENTION

Embodiments of the present invention are directed to an RF ablation catheter which gives lesion feedback of a more direct nature, at least tip-contact detection if not also tip-force, tissue thickness, and pre-pop warnings, and which is also preferably relatively inexpensive to manufacture. Advantageously, such an inventive device can be substantially smaller in French diameter than any near-term device based on the fiber-optic triple fiber (3 or more optical fibers) approach. Further, one could software-enable any one or more of these measurement capabilities. The lesion feedback may employ pulse-echo monitoring for monitoring and/or control of thermally ablative lesioning not only in nonlayered tissues but also in layered tissues such as cardiac muscle tissues and skeletal muscles.

In accordance with an aspect of the present invention, an ablation catheter with acoustic monitoring comprises an elongated catheter body extending longitudinally between a proximal end and a distal end along a longitudinal axis; a distal member disposed adjacent the distal end, the distal member including an ablation element to ablate a biological member at a target region outside the catheter body; and one or more acoustic transducers each configured to direct an acoustic beam toward a respective target ablation region and receive reflection echoes therefrom. The distal member includes a transducer housing in which the one or more acoustic transducers are disposed, the transducer housing including at least one transducer window which is the only portion in the distal member through which the acoustic beam passes, at least the at least one transducer window portion of the distal member being made of a material comprising at least 50% carbon by volume, the transducer window material being thermally and electrically conductive and having an acoustic impedance between an acoustic impedance of the one or more acoustic transducers and an acoustic impedance of the biological member.

In some embodiments, the transducer window material is at least about 90% carbon by volume. The transducer window material is about 100% carbon by volume. The transducer window material comprises a carbon matrix material which is exterior surface-infused with a noble metal. The transducer window material includes an exterior surface-infused or overlying coating of noble metal. The at least one transducer window spans 360 degrees around the one or more acoustic transducers. The distal member is made substantially entirely of the transducer window material. The distal member is made substantially entirely of carbon. The distal member comprises a surface coating of noble metal on an exterior surface thereof, and the distal member is more than about 90% by volume carbon. The transducer window material has an acoustic impedance of about 20-30 mega Rayles (kg/m2 s). The transducer window comprises an acoustic lens having a concave external surface.

In specific embodiments, the ablation apparatus further comprises a control unit configured to control the ablation element and the one or more acoustic transducers so that thermal ablation of the biological member and passage of the acoustic beam to and from the biological member occur sequentially and periodically. The control unit is configured to control the ablation element and the one or more acoustic transducers so that the thermal ablation of the biological member has a high duty cycle of more than about 90% and the directing of the acoustic beam passage to and from the biological member has a low duty cycle of less than about 10%. The one or more acoustic transducers include a sideways-directed acoustic transducer to monitor sideways-formed lesion and a forward-directed acoustic transducer to monitor forward-facing lesion, respectively. The distal member is rotatable to direct acoustic beam from the sideways-directed acoustic transducer through the at least one transducer window toward a target tissue on a side of the distal member. A remaining portion of the distal member, other than the at least one transducer window portion, comprises one or more materials selected from the group consisting of metal, ceramic, cermet, and glass.

In accordance with another aspect of the invention, an ablation catheter with acoustic monitoring comprises an elongated catheter body extending longitudinally between a proximal end and a distal end along a longitudinal axis; a distal member disposed adjacent the distal end, the distal member including an ablation element to ablate a biological member at a target region outside the catheter body; and one or more acoustic transducers each configured to direct an acoustic beam toward a respective target ablation region and receive reflection echoes therefrom. The distal member includes a transducer housing in which the one or more acoustic transducers are disposed, the distal member being made of a material comprising at least 50% carbon by volume, the distal member material being thermally and electrically conductive and having an acoustic impedance between an acoustic impedance of the one or more acoustic transducers and an acoustic impedance of the biological member.

Another aspect of the invention is directed to an acoustic monitoring method for an ablation procedure using an ablation catheter which includes an elongated catheter body extending longitudinally between a proximal end and a distal end along a longitudinal axis; a distal member disposed adjacent the distal end, the distal member including an ablation element to ablate a biological member at a target region outside the catheter body; and at least one acoustic transducer. The distal member includes a transducer housing in which the at least one acoustic transducer is disposed. The transducer housing includes at least one transducer acoustic window each corresponding to the respective at least one acoustic transducer, the at least one transducer acoustic window being the only portion in the distal member through which respective acoustic beam from the respective at least one acoustic transducer passes, the at least one transducer window being made of a material comprising at least 50% carbon by volume, the transducer window material being thermally and electrically conductive and having an acoustic impedance between an acoustic impedance of the at least one acoustic transducer and an acoustic impedance of the biological member. The method comprises thermally ablating the biological member at the target region with the ablation element; and directing an acoustic beam through the acoustic window to and from the biological member.

In some embodiments, directing the acoustic beam to and from the biological member comprises at least one of acoustic lesion feedback of the biological member being ablated, a tissue thickness measurement in a region of the biological member being ablated, a tissue proximity measurement in a region of the biological member being ablated, a pre-pop warning of the biological member being ablated, a pre-pop detection of the biological member being ablated, or sensing of a tissue contact force on the distal member. The thermally ablating the biological member and the directing the acoustic beam to and from the biological member occur sequentially and periodically. The thermally ablating of the biological member has a high duty cycle of more than about 90% and the directing of the acoustic beam to and from the biological member has a low duty cycle of less than about 10%.

Another aspect of the present invention is directed to a method of monitoring ablative progress of a layered tissue having preexisting tissue interfaces during thermal ablation of the layered tissue utilizing acoustic pulse-echo feedback. The method comprises: prior to thermal ablation of the layered tissue, directing an acoustic pulse-echo beam to the layered tissue to obtain pre-ablation acoustic reflections from the layered tissue; thermally ablating the layered tissue; during thermal ablation of the layered tissue, directing an acoustic pulse-echo beam to the ablated layered tissue to obtain acoustic reflections from the ablated layered tissue for acoustic pulse-echo feedback; and comparing the acoustic reflections from the ablated layered tissue with the pre-ablation acoustic reflections to assess the ablative progress of the ablated layered tissue. The ablative progress includes at least one of a change in acoustic reflectivity from the preexisting tissue interfaces of the ablated layered tissue relative to the pre-ablation acoustic reflections, appearance of one or more new acoustically reflective regions not associated with the preexisting tissue interfaces based on a change in acoustic reflectivity in the one or more new acoustically reflective regions, or an amount of edema swelling indicated by an increase in a lesion depth or a lesion volume based on the acoustic reflections from the ablated layered tissue.

In some embodiments, assessing the ablative progress of the ablated layered tissue comprises monitoring the acoustic reflections from the preexisting tissue interfaces to identify initiation and growth of ablative micro-bubbling. Assessing the ablative progress of the ablated layered tissue comprises monitoring the acoustic reflections from regions not associated with the preexisting tissue interfaces to identify initiation and growth of ablative micro-bubbling. Assessing the ablative progress of the ablated layered tissue comprises monitoring the acoustic reflections from the preexisting tissue interfaces to identify an increase in swelling-related distances between the preexisting tissue interfaces to indicate edema.

In specific embodiments, the thermal ablation and the acoustic pulse-echo feedback are performed with an ablation and monitoring device having an ablation element and an acoustic transducer, and the method further comprises fixing a position of the ablation and monitoring device with respect to the layered tissue during the thermal ablation and the acoustic pulse-echo feedback. Fixing the position of the ablation and monitoring device comprises vacuum clamping the ablation and monitoring device to the layered tissue. The thermal ablation and the directing of the acoustic pulse-echo beam to the ablated layered tissue occur simultaneously. The thermal ablating and the directing of the acoustic pulse-echo beam to the ablated layered tissue occur sequentially and periodically. The thermally ablating has a high duty cycle of more than about 90% and the directing of the acoustic pulse-echo beam to the ablated layered tissue has a low duty cycle of less than about 10%. The acoustic pulse-echo beam has a frequency of about 6-10 MHz. The thermal ablating is performed using a HIFU (High Intensity Focused Ultrasound) transducer and the directing of the acoustic pulse-echo beam is performed using the same HIFU transducer.

Another aspect of this invention is directed to an ablation and monitoring apparatus for monitoring ablative progress of a layered tissue having preexisting tissue interfaces during thermal ablation of the layered tissue utilizing acoustic pulse-echo feedback. The ablation and monitoring apparatus comprises: a distal member disposed adjacent a distal end of a catheter body; an ablation element disposed in the distal member to ablate a layered tissue at a target region outside the catheter body; an acoustic transducer disposed in the distal member and configured to direct an acoustic pulse-echo beam toward the target region; a control unit coupled to the ablation element and the acoustic transducer to control the ablation element and the acoustic transducer so as to, prior to thermal ablation of the layered tissue, direct an acoustic pulse-echo beam to the layered tissue to obtain pre-ablation acoustic reflections from the layered tissue, and during thermal ablation of the layered tissue, direct an acoustic pulse-echo beam to the ablated layered tissue to obtain acoustic reflections from the ablated layered tissue for acoustic pulse-echo feedback; and an analyzer coupled to the acoustic transducer and configured to compare the acoustic reflections from the ablated layered tissue with the pre-ablation acoustic reflections to assess the ablative progress of the ablated layered tissue. The ablative progress includes at least one of a change in acoustic reflectivity from the preexisting tissue interfaces of the ablated layered tissue relative to the pre-ablation acoustic reflections, appearance of one or more new acoustically reflective regions not associated with the preexisting tissue interfaces based on a change in acoustic reflectivity in the one or more new acoustically reflective regions, or an amount of edema swelling indicated by an increase in a lesion depth or a lesion volume based on the acoustic reflections from the ablated layered tissue.

In some embodiments, the thermal ablation and the acoustic pulse-echo feedback are performed with an ablation and monitoring device having an ablation element and an acoustic transducer, and the apparatus further comprises a mechanism to fix a position of the ablation and monitoring device with respect to the layered tissue during the thermal ablation and the acoustic pulse-echo feedback. The mechanism comprises a vacuum clamping mechanism. The control unit controls the ablation member and the acoustic transducer to perform the thermal ablating and the directing of the acoustic pulse-echo beam to the ablated layered tissue simultaneously. The control unit controls the ablation member and the acoustic transducer to perform the thermal ablating and the directing of the acoustic pulse-echo beam to the ablated layered tissue sequentially and periodically.

These and other features and advantages of the present invention will become apparent to those of ordinary skill in the art in view of the following detailed description of the specific embodiments.

BRIEF DESCRIPTION OF THE DRAWINGS

FIG. 2 is a schematic diagram of an ablation apparatus incorporating the ablation catheter tip of FIG. 1 or FIG. 1A.

DETAILED DESCRIPTION OF THE INVENTION

Figure 1:
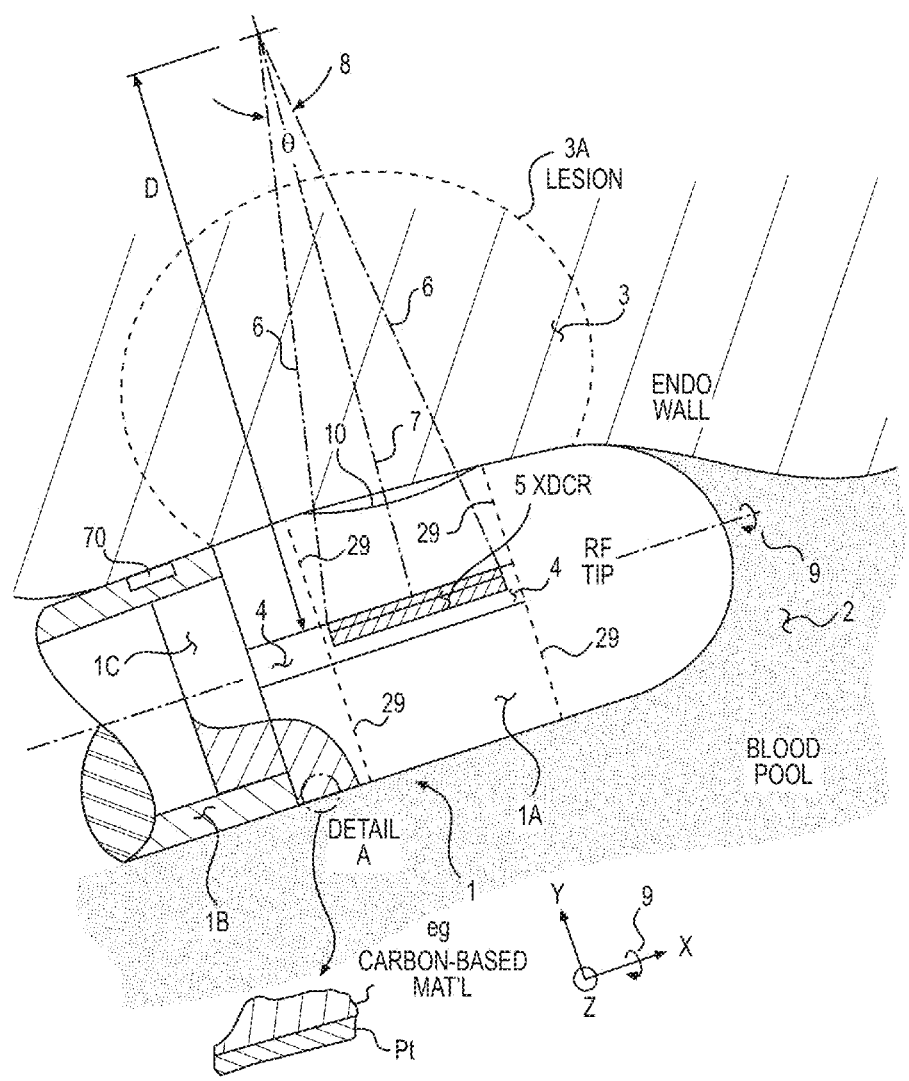
FIG. 1 is a schematic view illustrating an ablation catheter tip placed against a tissue surface or endocardium to produce thermal ablation according to a single transducer embodiment of the present invention.

In the following detailed description of the invention, reference is made to the accompanying drawings which form a part of the disclosure, and in which are shown by way of illustration, and not of limitation, exemplary embodiments by which the invention may be practiced. In the drawings, like numerals describe substantially similar components throughout the several views. Further, it should be noted that while the detailed description provides various exemplary embodiments, as described below and as illustrated in the drawings, the present invention is not limited to the embodiments described and illustrated herein, but can extend to other embodiments, as would be known or as would become known to those skilled in the art. Reference in the specification to "one embodiment," "this embodiment," or "these embodiments" means that a particular feature, structure, or characteristic described in connection with the embodiment is included in at least one embodiment of the invention, and the appearances of these phrases in various places in the specification are not necessarily all referring to the same embodiment. Additionally, in the following detailed description, numerous specific details are set forth in order to provide a thorough understanding of the present invention. However, it will be apparent to one of ordinary skill in the art that these specific details may not all be needed to practice the present invention. In other circumstances, well-known structures, materials, circuits, processes and interfaces have not been described in detail, and/or may be illustrated in block diagram form, so as to not unnecessarily obscure the present invention.

In the following description, relative orientation and placement terminology, such as the terms horizontal, vertical, left, right, top and bottom, is used. It will be appreciated that these terms refer to relative directions and placement in a two dimensional layout with respect to a given orientation of the layout. For a different orientation of the layout, different relative orientation and placement terms may be used to describe the same objects or operations.

Exemplary embodiments of the invention, as will be described in greater detail below, provide one or more acoustic transducers in or adjacent a thermal ablation tip for lesion feedback, catheter tip-contact and force monitoring, tissue thickness measurement, and pre-pop warning. In specific embodiments, the lesion feedback involves pulse-echo monitoring and control of thermally ablative lesioning in layered tissue.

Acoustic Transducer(s) in or at an Ablation Catheter Tip

FIG. 1 is a schematic view illustrating an inventive ablation catheter tip placed against a tissue wall (e.g., endocardial wall) to produce thermal ablation according to an embodiment of the present invention. The ablation catheter tip in the first major embodiment is a carbon-based RF tip and in a second major embodiment is a cored thermally and electrically conductive metal or ceramic tip. In a macroscopic manner, either embodiment acts thermally and electrically generally like a conventional platinum-iridium alloy metal-tip catheter yet has the echo-pinging capability. In the first carbon-based embodiment the acoustical energy can pass through the carbon tip material; thus the transducer can be buried beneath it without requiring coring of the carbon. However, coring may also be used with carbon-body tips. In both the carbon first embodiment and the cored metal or ceramic second embodiment, the respective tips may contain, most typically, either a single transducer or dual transducers aimed in different directions of ablation.

As seen in FIG. 1, the distal portion of the catheter 1 is placed against a tissue wall 3 in order to deliver a lesion 3a and is otherwise immersed in the chamber blood pool 2. The ablating and data-gathering catheter 1 of FIG. 1 has an RF ablation tip 1a with a smaller-diameter mating boss 1c which fits into a polymeric catheter lumen body 1b. A tip coordinate system is shown in the lower right of the figure and the catheter tip axis is generally arranged along or parallel to the x-axis. The RF ablating tip 1a/1c of FIG. 1 is depicted as having a slot or chamber 4 which contains an ultrasonic transducer 5. The transducer 5 is shown having two layers, typically comprised of a piezoceramic and an acoustic matching layer as is known in the art. The transducer 5 is arranged to fire a preferably focused ultrasound beam 6 along or parallel to the +y-axis, the pinging beam shown having a focus at a distance D from the transducer 5. The pinging beam has an included angle θ shown as item 8. A mechanism 70 such as a vacuum clamping mechanism may be provided to fix the position of the distal member of the catheter (RF ablating tip 1a/1c) to the tissue being ablated by vacuum or the like. Note that FIG. 1 depicts an uncored carbon based tip 1a having a single side-looking (+Y direction) transducer 5 capable of providing echoes from side-formed lesion 3a.

The ablation tip 1 preferably allows for the ablating tip 1a to be rotated about the x-axis with a rotation such as rotation 9. The tip rotation allows for directing a directional pinging transducer such as transducer 5 toward the tissue. This rotation, in one preferred embodiment, is independent of the extended catheter body 1b. In other words, the transducer/tip 1a can be rotationally pointed or oriented about the x-axis with rotation 9 preferably (but not necessarily) without rotating the catheter body 1b itself. This avoids the situation where the catheter guidewire bending motions interfere with desired tip rotational movements. That problem happens when trying to bodily twist a catheter which has been bent into shape using bending wires (the catheter no longer twists completely on its own axis but rotates bodily in its deformed shape). Note that if the transducer 5 were alternatively annular or ring shaped with its axis aligned along the tip x-axis and directing acoustical energy about its 360 degree surroundings into y-z planes (not shown), it would then not need to be physically rotated about the x-axis. Tip rotation mechanisms are known in the art. See, e.g., U.S. Pat. Nos. 7,666,143 and 7,678,056, which is incorporated herein by reference in its entirety.

The catheter tip 1a/1c, in the first major embodiment, comprises substantially a carbon-based material, such as materials available from companies including POCO. Carbon-based materials have a nice combination of thermal conductivity and electrical conductivity, and as the inventors have determined, a helpful intermediate acoustic impedance between that of the transducer and that of the tissue. Fine grained carbon materials are quite strong and can receive a fine finish. Thus, such carbon materials appreciably have the thermal and electrical properties of the platinum-iridium metal they are replacing but even more critically have the acoustic transmissivity and low acoustic reflection attributes necessary to transport acoustical energy into and through the carbon material. Platinum-iridium of any appreciable thickness (thousands of angstroms or more) is acoustically reflective due to its high acoustic impedance so that it would not allow ultrasound to easily exit or reenter the tip. The use of carbon at a much lower acoustic impedance than platinum means a low and desirable acoustic reflection coefficient (i.e., a high acoustic transmissivity).

Thus, the transducer 5 can fire its beam and receive echoes therefrom through the bulk carbon material of the carbon tip 1a with minimal acoustic reflections and losses at the transducer/carbon interface and at the carbon/tissue interface. This is a huge improvement over an ablation tip where the predominant overlying tip material is a metal such as platinum-iridium (PtIr). In that case the transducer would not be operable through such a metal of more than a few thousand angstroms thick because of the unavoidable impedance-mismatch induced reflections. Thus, the carbon based tip allows for a tip which is all carbon on the outside and has the transducer hidden and protected inside (per FIG. 1). The carbon, from an electrical and thermal viewpoint, substantially acts like the platinum bulk metal it replaces. By "substantially" we mean that reasonable tip operating peak temperatures of about 60-80 Deg C. can still be attained with irrigation flow and that voltage drops within the carbon RF electrode are acceptable.

In order to retain the equivalent full historic function of platinum-iridium tips, it may be advantageous to coat the carbon tip 1a with a thin sputtered thin film of platinum, platinum-iridium, rhodium, or gold as depicted in detail A in FIG. 1. Note that the overlying metal thin film need only be very thin (perhaps 800-1000 angstroms). Its function is mainly to offer a familiar electrical work-function and chemical behavior in contact with tissue and blood. Preferably a known thin film adhesion layer of several hundred angstroms (or more) of titanium or chromium (not shown) is employed between the carbon and the platinum-based overcoat. This provides extremely strong adhesion during thermal cycling and abrasion as is known in the thin film deposition art. One could sputter coat hundreds of tips in one deposition chamber pump down to minimize cost. As long as the platinum coating is about 1000 angstroms thick or less, its negative acoustic consequences can be tolerated. Alternative thin coating metallic materials might include alloys of gold, rhodium, platinum and iridium.

The challenge to doing acoustic lesion feedback is placing an acoustic transducer in/on an RF ablation tip such that (a) the beam has an acoustic window into/out of the tip, and (b) one does not destroy the substantial thermal and electrical conductivity of the historic solid-body PtIr tip or its overall toughness. The thermal conductivity is particularly critical in order to prevent the tip from itself overheating and charring (as opposed to thermally necrosing) adjacent tissue. Saline will typically be flowed through such a tip (saline paths not shown in FIGS. 1 and 1a) to provide such conductive tip-cooling in the form of an "irrigated catheter." The inventors recognized that a carbon based engineering material has substantial thermal and electrical conductivity, good strength, as well as low acoustic attenuation, good midrange intermediate acoustic impedance-bridging between PZT and to tissue and a possibility of simultaneously serving as an acoustic focusing lens such as by using a lens shaped surface 10 in FIG. 1. The inventors further realized that such a carbon-based tip could easily be sputter coated with platinum or platinum iridium such that from the outside one sees a very similar functionality as an historic solid platinum-alloy metal RF tip. Such a carbon-based acoustic sensing tip can perform RF ablation and thickness and lesion detection as well as tip-force contact monitoring.

Figure 1A:
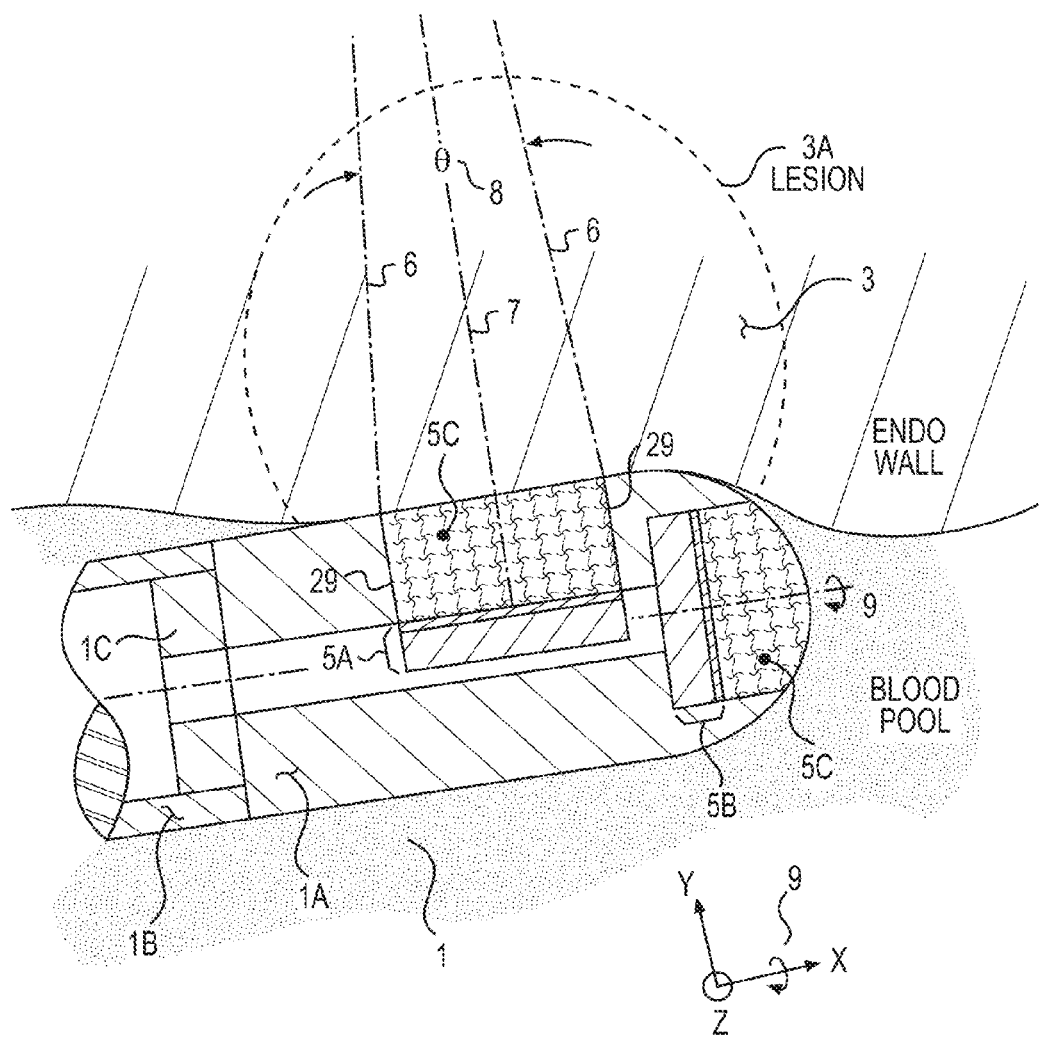
FIG. 1A is a schematic view illustrating an ablation catheter tip placed against a tissue surface or endocardium to produce thermal ablation according to a dual transducer embodiment of the present invention

We again note, for simplicity, that in FIGS. 1 and 1a we have not depicted fluid cooling lumens or electrical interconnects to operate the transducers or thermocouples or thermistors to monitor tip temperature, all of which are widely known in the catheter art.

The second major embodiment, as mentioned earlier, utilizes a tip material substantially comprising the historic platinum-iridium or a thermally and electrically conductive metal or glass rather than substantially carbon. Such materials in bulk form will not efficiently pass ultrasound emitted from a piezotransducer because of unacceptable acoustic reflections (unlike the earlier carbon embodiment), so a physical window must be provided in these materials for ultrasound to pass outward and inward. This is done by coring into the tip material. In order to preserve the outward functionality of today's platinum-iridium tips, it may be sputter coated with platinum iridium at least in regions not already comprised of platinum iridium. Because the thermally and electrically conductive metal, ceramic or glass can pass heat and electrical current and because it has an outer platinum-iridium surface, it globally or macroscopically functionally acts like a conventional platinum-iridium tip. Examples of suitable tip metals include titanium alloys, nickel alloys, and stainless steels, all of which have some useful biocompatibility even in uncoated form.

Recall that FIG. 1 illustrates in solid lines the case where the transducer 5 is mounted in a slot 4 and the acoustic beam passes through the bulk tip material (carbon in the first major embodiment). FIG. 1 also depicts a shallow concave acoustic lens 10 formed in the carbon surface of the tip 1a. In this variation of a carbon tip, the transducer is well-buried inside bulk carbon.

FIG. 1 also illustrates in phantom lines 29 the alternative second major embodiment (a cored tip). The phantom lines 29 outline a cored or drilled diameter along the y-axis within which the transducer 5 is mounted. Such a cylindrical (or other shaped) through-hole or blind-hole depicted by the phantom lines 29 may be drilled by EDM (Electrical Discharge Machining), precision twist drill, or laser, for example. Powder metallurgy may also be utilized to form such a tip. Such a hole arrangement allows for the use of a tip bulk-material which is not acoustic-friendly (e.g., it is acoustically opaque or highly reflective such as thick platinum, stainless, or titanium). This is because after the transducer 5 is placed in the hole 29 (see also FIG. 1A) one could overlay the transducer with a hole-plug or hole-cap of acoustic-friendly material such as a urethane or carbon, or an epoxy acoustic lens. If necessary, the exposed face of that filled hole 29 on the tip outer-surface may also be overcoated with thin platinum-iridium to assure electrical conductivity and even some thermal conductivity across the face of such a filling plug. "Thin" means on the order of a few hundred to a few thousand angstroms as these thicknesses can pass appreciable acoustics. Note that the functionally ideal case is when the transducer 5 is well-buried and is overlaid with a thick bulk of thermally conductive and electrically conductive material (such as carbon or a metal). Such a tip only needs a very thin platinum coating to offer the familiar platinum work-function and biochemical compatibility. Such complete burial or physical protection of the transducer 5 can be achieved by placing it in a slot of the type 4 or by placing it in a hole 29 and overlaying it with a thick, relatively water-impermeable material such as epoxy or polycarbonate that has the desired acoustic impedance and low attenuation. Note that either a slot 4 structure or a hole 29 structure may utilize either a carbon-based body or a thermally/electrically conductive metal or ceramic body. Thus, in the second embodiment we fill the hole 29 with a transducer and its overlying protective, acoustically transparent covering.

The tip 1a may alternatively be constructed, for example, as two minor-image halves split down the x-z plane (not shown). This allows for easy transducer mounting and wiring despite using a slot-like cavity 4. The two facing halves, segments or layer portions are bonded together face-to-face. By face-to-face is meant that the two halves face each other but are not necessarily in intimate direct contact with each other. The two halves may, for example, be fused or bonded together with a film of reflowed glass, reflowed metal-loaded glass frit, epoxy, conductive epoxy, or solder, for example, or even laser-welded or resistance-welded at the exposed edges. One (or both) of those halves may contain the relief-space for the transducer 5.

FIG. 1A illustrates an inventive second-embodiment cored-tip having dual transducers wherein the tip material is a thermally conductive metal, ceramic or glass as described above. Again a side-fire transducer 5a performs pulse-echo pinging into a side-forming lesion 3a. As with most RF ablation tips the tip may alternatively form forward-facing lesions (none shown) and in that case the forward-facing transducer 5b is also provided for when ablation is performed end-on (only sideways ablation depicted). Note that both transducers 5a and 5b are mounted in cored holes which are substantially backfilled with acoustically transparent window material 5c such as a urethane or polymer. The material 5c might also include an acoustic lens and/or a thin metallic overlying RF electrode material such as that used in the first embodiment to coat carbon, for example.

Within our scope is the use of a single transducer directed at an angle between those of FIG. 1A (e.g., at 45 degrees to the tip longitudinal axis (not shown)). A single 45 degree (or approximately 45 degree) transducer will have some field of view of both forward-made lesions and of sideways-made lesions. Also within the scope is the use of tip contact-angle-to-tissue information to correct for the fact that a transducer is not looking orthogonal or normal into tissue. Such tip-angle information can be obtained from 3D navigation systems such as the St. Jude Medical Ensite System and the Biosense Webster Carto system. This is particularly useful in the above single-transducer 45 degree configuration.

Transducers 5 and 5a of the inventive ablation device may serve one or more of several functions as follows:

a) Lesion Feedback. The transducer 5, 5a can perform pulse-echo assessment of a forming or formed lesion such as the assessment of the depicted RF side-lesions 3a. Several acoustic parameters vary with lesion-formation including increasing attenuation, increasing reflections and increased scattering from nucleated micro-bubbles and desiccated cross-linked tissue. Preferably the lesion is pinged during periods when ablation is stopped temporarily to reduce electrical interference issues between ablation and pinging. Ideally one would obtain a pre-lesion baseline ping and observe increases in acoustic reflectance as lesioning proceeds in steps. Note that the transducer beam is perfectly aligned down the center of the lesion 7 since the ablator and the pinger are co-registered in a single tip; there are no alignment issues or distorted-view issues. Ideally the pinging periods are short enough that significant lesion cooling does not occur before RF ablation power restarts, such as pinging periods of 0.1-100 milliseconds in length during which an averaged low-noise return signal can be computed from numerous individual pings.

b) Tissue Thickness and Proximity. Similar pulse-echo pinging allows for the distance/thickness measurement of tissue interfaces and layers. If the RF tip is placed against the tissue wall (as shown), these additional echoes will be from interior layers and interfaces (not shown) such as the muscle striations and the epicardium and epicardial/pericardial interfaces. Again the transducer looks down the center of the lesion and is self-aligned with it. Tissue walls such as the endocardium or pulmonary vein ostia which are millimeters or centimeters distant from a pre-contacting tip across blood are easily distinguished in the ping reflections because the intervening blood itself has virtually no echo.

c) Tip Contact Force. The inventors have done work to demonstrate that one can deduce ablator tip force on tissue from changes in a resonant or antiresonant property of a platinum-iridium tip. This should also be true of carbon-based, metal and ceramic tips albeit at different resonant frequencies because of the tip-material change. More specifically, one may use the transducer 5, 5a to excite some tip resonances (usually there is at least one resonance peak for each primary dimension of the tip such as the tip diameter, tip circumference and tip length). Although the tip chamber 4 will modify the resonance spectrum of the tip from a non-chambered tip, one can still easily see changes in that tip vibrational spectrum due to tip-loading. One or more such modal peaks or minima may be watched for amplitude and/or frequency changes as a function of tip force. Such changes can be calibrated to known forces during product development. Ideally two or more peaks or minima are employed, one being sensitive to axial loading and the other to radial loading. Ideally the tip also contains a thermocouple or thermistor for measuring tip temperature and possibly also for correcting the acoustic feedback for temperature. Note that the transducers, for purposes of contact-force deduction, may excite the tip at tip resonant and/or antiresonant frequencies different from the resonant frequencies of the transducers themselves. Typically the tip resonances are lower in frequency than the transducer resonances because of the tip's larger dimensions.

d) Pre-pop Detection and Avoidance. The depicted tips 1a will easily be able to detect a pre-pop condition which is a rapidly growing bubble layer or bubble-cloud just under the tissue surface adjacent the tip 1a. Such a bubbling eventually-delaminating area suddenly and temporarily (until bubble collapse) gives a huge acoustic echo and will actually block any echoes coming from deeper than the superficial bubbling delaminating pre-pop region. One may configure the ablation device such that it turns its own power off or down to prevent an audible (or even inaudible) pop event. The inventors have seen that large audible steam pop events are always preceded by smaller inaudible events, and that the preceding inaudible yet acoustically detectable "prepop" events can be employed to reduce power and avoid the larger dangerous and more tissue-damaging audible pop.

It will be noted that the transducer 5 of FIG. 1 is buried a distance beneath the tip surface 10. This spacing acts as an acoustic standoff known in the acoustic arts to favorably remove nearfield transducer reverberations from the earliest received acoustic echoes. One may additionally or alternatively be able to acoustically monitor the bubbling and/or cavitation noises caused by the prepop bubbling phenomenon.

One may utilize the various types of data feedback from the catheter tip in several manners. Here are some examples.

1) One or more parameters taken individually are used to advise or inform the practitioner.

2) Two or more parameters are combined and at least one resulting third parameter is used to advise or inform the practitioner.

3) One or more parameters taken individually are used as an interlock, limit, or shutoff to automatically prevent an aspect of undesirable operation.

4) Two or more parameters are combined and at least one resulting third parameter is used as an interlock, limit, or shutoff to automatically prevent an aspect of undesirable operation.

5) One or more parameters taken individually are used to provide feedback to the operation of the system, possibly without user involvement.

6) Two or more parameters are combined and the resulting at least one third parameter is used to provide feedback to the operation of the system, possibly without user involvement.

7) Any number of parameters are combined in an algorithm to make a decision or recommendation regarding the intended, actual or delivered treatment or the patient's condition, the algorithm operating anywhere including in a console or on a network, the decision or recommendation being made to the patient, to a practitioner, or to the system software or hardware itself.

8) A robot manipulates at least the tip portion and utilizes one or more parameters to deliver a treatment or assess a lesion or the patient's condition. The robot may utilize its own articulator or introducer to hold the tip in place against the tissue.

9) The inventive device is tracked on a spatial navigation system.

10) The inventive device is tracked using one or more on-catheter or off-catheter diagnostic imaging devices.

As a reminder a parameter could be, for example, any one of contact force, a tip-related temperature, power, time, fluid flow rate, lesion size or depth, tissue thickness, tissue proximity, tip sideways versus forward orientation, any prepop related parameter such as a reflectivity amplitude or intensity, a rate of change of any of the above, or an algorithmic combination of any of the above.

FIG. 2 is a schematic diagram of an ablation apparatus incorporating the ablation catheter tip of FIG. 1 or FIG. 1A. An ablation catheter 110 includes a control handle 116, and an elongated catheter body 112 having a distal region 114 adjacent a distal end 118. The distal region 114 includes any of the ablation tips shown and described above. The catheter 110 is connected with an ablation energy source 120 such as an RF generator, and with an irrigation fluid source 124 to provide an irrigation and tip-cooling fluid. A transducer pinger 128, which might have more than one channel, supplies pinging energy such as electrical energy pulses to the acoustic transducer(s) 5, 5a, 5b. A control unit 130 is provided for controlling the ablation and the acoustic pinging during ablation. For instance, the control unit 130 is configured to carry out the duty cycles for ablation and pinging. An acoustic pinger echo analyzer 132 is provided to condition and analyze the data collected by the acoustic transducer 5, 5a, 5b to provide one or more of lesion feedback, tissue thickness or proximity measurement, tip contact force monitoring, and pre-pop detection. The information is preferably presented to the operator (e.g., using a graphical user interface) to provide real time assessment of the ablation. The information may additionally or alternatively be utilized by the system itself without operator intervention.

Based on the features described above, one aspect of the invention is directed to an RF ablation catheter with one or more acoustic transducers therein or thereon, wherein the acoustic transducer(s) is capable of at least one of acoustic lesion feedback, catheter tip-force monitoring, tissue thickness or proximity measurement, or pre-pop warning. The catheter is capable of delivering an RF ablating tip to a patient's tissue to be ablated. In the first major embodiment, the tip is substantially comprised of a carbon or carbon-based material. The carbon-based tip contains or supports at least one acoustic transducer. The transducer is operable to perform at least one of lesion feedback, tip-force feedback, tissue-thickness or proximity feedback, or pre-pop warning or protection. The carbon material may be utilized as an acoustic window, standoff or lens, or as an electrode to operate the transducer, or to isolate the transducer from the tissue or blood. The carbon tip may have the transducer enclosed within it, mounted on it or otherwise contained within its outer boundaries whose acoustic beam passes through at least some of the carbon material. Alternatively, the carbon tip may have the transducer mounted in it or enclosed in it or otherwise contained within its extreme boundaries whose acoustic beam passes through a second material different from the carbon material, wherein the second material is placed between the tissue and the transducer. In specific embodiments, the carbon catheter tip has any of the following features: (a) an internal (preferred) or external cavity for an acoustic transducer, (b) a shaped surface which acts as an acoustic lens, (c) a thermistor, thermocouple or other temperature detector, and (d) a partial or complete overcoat of a thin film noble metal.

In the second major embodiment, the ablation tip substantially comprises a thermally and electrically conductive metal, ceramic or glass such as a titanium alloy, stainless alloy or cermet. The metal, ceramic or glass-based tip contains or supports at least one acoustic transducer. The metal, ceramic or cermet material, in bulk form, may not be utilized as an acoustic window, standoff or lens because it has poor acoustic impedance-matching to the transducer and/or tissue. It may have a transducer mounted in it or enclosed in it or otherwise contained within its extreme boundaries as within a bore hole whose acoustic beam passes through a second acoustic-friendly material filling the bore hole different from the metal, ceramic or glass material, wherein the second material is placed between or fills the space between the tissue and the transducer. The metal, ceramic or glass catheter tip has any of the following features: (a) an internal or external cavity for an acoustic transducer, (b) a thermistor, thermocouple or other temperature detector, (c) a partial or complete overcoat of a thin film noble metal, and (d) a through-hole or blind hole for transducer mounting. We include cermets, which are ceramic-metal composites, in the tip material list above.

In some first embodiments, the carbon material is at least in part overcoated or surface-infused (if porous) with a noble metal or alloy such as platinum, platinum-iridium or gold. The transducer emits and/or receives acoustical energy in any one or more of (a) a directed manner, (b) a directable manner, (c) an omni-directional manner, or (d) a manner coordinated with the delivery or stoppage of ablating RF energy. The catheter may also be utilized to pace tissue and/or sense tissue EP voltages or currents such as by using the RF electrode for that (with appropriate switching and isolation) or by using a second dedicated diagnostic electrode as is known in the ablation art (not shown). For a directed transducers such as side-firing transducers 5 and 5a of FIGS. 1 and 1a one would provide x-axis rotation of the directed transducer (or transducer plus surrounding tip) for aiming purposes as described above. This is preferably done without rotating the catheter body itself such as by an internal torque wire capable of ±180 degree movement.

Any one or more of tissue-thickness or proximity measurement, tip-force measurement or lesion-assessment measurement such as for a lesion-baseline reading may be made before ablating a particular tissue target. Any of tissue-thickness and proximity measurement, tip-force measurement, lesion assessment measurement or pre-pop measurement or lesion-feedback may be made during or after an RF ablation is carried out. The measurement(s) may take place (a) while the RF ablating power is on, (b) while the RF ablating power is turned off, (c) while the RF ablating power is turned off and a waiting period has passed, or (d) before the RF ablating power is turned on again. The inventors have noted that, after RF ablation is turned off, a short relaxation time decreases micro-bubble concentrations thereby allowing echoes due to desiccation to be more apparent. Either or both of bubble and desiccation-related echoes can be employed to monitor lesioning.

The catheter may be delivered into the patient using an intravascular approach, an intrapericardial approach, a subxiphoid approach, or a trans-thoracic approach, for example. The ablation site or sites may be on an endocardial surface, on an epicardial surface, and/or within any cardiac-associated tissue including the pulmonary veins. The catheter has a handle and that handle includes at least one of: (a) at least one catheter bending actuator, (b) at least one catheter or catheter-tip rotating actuator, and (c) at least one control to activate any one or more of an RF ablation, a tip force measurement, a lesion feedback measurement, or a tissue thickness or proximity measurement.

The transducer is comprised of any one or more of: (a) a single crystal piezomaterial, (b) a polycrystalline piezomaterial, (c) a piezopolymer material, (d) a magnetostrictive material, (e) an electrostrictive material, (f) a MEMS-based transducer, (g) any type of electrostatic transducer, (h) a CMUT transducer, and (i) a thin-film or thick-film or sol-gel based piezo-transducer. The transducer may have one or more overlying acoustic matching layers. The transducer may be further overlaid with an acoustically transparent low-reflection acoustic window or lens made of a material different from the metal, ceramic or glass based tip. The acoustic window or lens may be made from or may include any one or more of the following materials having the desired acoustic impedance: (a) epoxy or epoxy-matrix based material, (b) carbon or carbon-matrix based material, (c) glass, (d) rubber, silicone or urethane-including or based material, (e) an acoustically transmissive polymer such as polycarbonate, polystyrene or TPX, (f) a ceramic such as machinable ceramic Macor® or photosensitive-wet-etched glass-ceramic.

Pulse-Echo Monitoring and Control of Thermally Ablative Lesion in Layered Tissue The inventors have discovered that attempting to track the formation of a thermally ablative lesion in layered tissue is different from that in nonlayered tissue and that edema which occurs in nonlayered or layered living tissue being ablated can also be quantified to at least further ease the complexity of lesion tracking in living tissues. The edema phenomenon does not take place in nonliving, nonperfused bench tissue specimens. Edema or swelling quantification itself can also contribute to assessing a state of lesioning. Heart muscle tissues, for example, are layered in structure; as are muscles which allow arm and leg movement. Each such muscle layer comprises its own slab or bundle of bound muscle fibers with the different layers of the overall sandwich being less bound to each other and having discrete fluid-containing infused or lubricated interfaces between them. The inventors have discovered that acoustic pinging of preablation living layered tissues clearly depicts the echoes of these preexisting muscular layer interfaces even before lesioning. The inventors have also discovered that thermal ablation which occurs in living tissue containing one or more such layer(s) preferentially causes increasingly larger amplitude acoustic reflections from such interfaces as they are ablated. In other words, one observes growing reflections from the known preexisting interfaces during ablation whereas one sees less or minimal new ablation-related reflections from tissue where there was no known preexisting layer interface. The following discusses why that is the case.

It is known that micro-bubbles are more easily nucleated in interfaces, particularly liquid containing interfaces. This is due to the lack of nucleation and growth constraints which would have been imposed by enveloping surrounding and containing tissues. It is believed that most of the increased reflections from ablated layered tissue come mainly from its interfaces and include micro-bubbles growing mainly in those interfaces. Of course we also see contrast due to desiccation and collagen crosslinking and these phenomena are all superimposed. The desiccation and crosslinking reflective increases seem permanent. The bubbling phenomena are mostly temporary wherein a significant portion of at least the larger bubbles disappear after RF power is off for seconds and at most for a few minutes. Both mechanisms are still indicative of that tissue region having reached critical temperatures for necrosis and bubble nucleation respectively.

Edema is the filling or inflating (swelling) of damaged or insulted tissues with water or other bodily liquid. Edema causes physical swelling and is a natural bodily response to injury. Tissue is insulted by ablation heat regardless of source and is likely also somewhat additionally damaged by the non-heat aspects of ablation sources such as the acoustic shockwaves of HIFU ablation or the RF current of the RF ablator described herein. Thus it is certainly fair to expect edema or swelling of a lesion site in response to the deposition or passage of such ablating energy itself as well as from the ablative heat that energy generates. The edema may be mainly in response to cellular damage or disruption caused by the ablating energy/heat but the point is that it is directly related to the act of ablating. Indeed one sees tissue swelling or edema in response to ablating. If one has a stackup of multiple muscular sublayers as one does in the heart wall or leg-thigh of an animal, one can visually watch the sandwich of layers actually physically swell in individual and overall total thickness via acoustic pulse-echo techniques or "pinging." The inventors have observed this swelling or edema cause anywhere from 5 to 25% increase in the total laminate sandwich thickness over a few minutes during and after an ablation. Hotter tissues generally have higher acoustic velocities by several percents but that effect would decrease the apparent acoustic-determined thicknesses over an ablation. The same applies to acoustic velocity increases because the tissue is necrosed (as opposed to fresh and nonablated tissue). Such few-percent velocity increases would tend to reduce the apparent acoustic thicknesses. Thus the edema appears to dominate and overwhelm these other smaller effects as the stacked layers grow in actual thickness (while swollen) as opposed to apparent thickness as demonstrated by the net acoustically measured thickness.

The inventors have ablated numerous living and dead tissues and have demonstrated that the edema effect only occurs in living tissues. On the other hand, not surprisingly, the pinging detects the preexisting tissue interfaces regardless of whether the tissue is live or dead. The preference for micro-bubbles to nucleate and grow at such muscle-layer interfaces is similar whether the tissue is live or dead but the living tissue certainly has a better source of fluids which can nucleate bubbles and/or conduct heat into adjacent muscle tissue layers. The inventors have made ablation lesions using both RF and HIFU, saved the pinging data, and sectioned the lesions to determine their sizes. The main difference is that RF is surface applied so that RF lesions are generally shallower than HIFU lesions and hence involve less total edema. For both RF and HIFU ablation, the individual tissue muscle layers in the endocardium can be seen by pinging, but obviously for RF and its shallower lesions, one burns fewer layers deep and also markedly burns the near surface unlike in HIFU.

Figure 3:
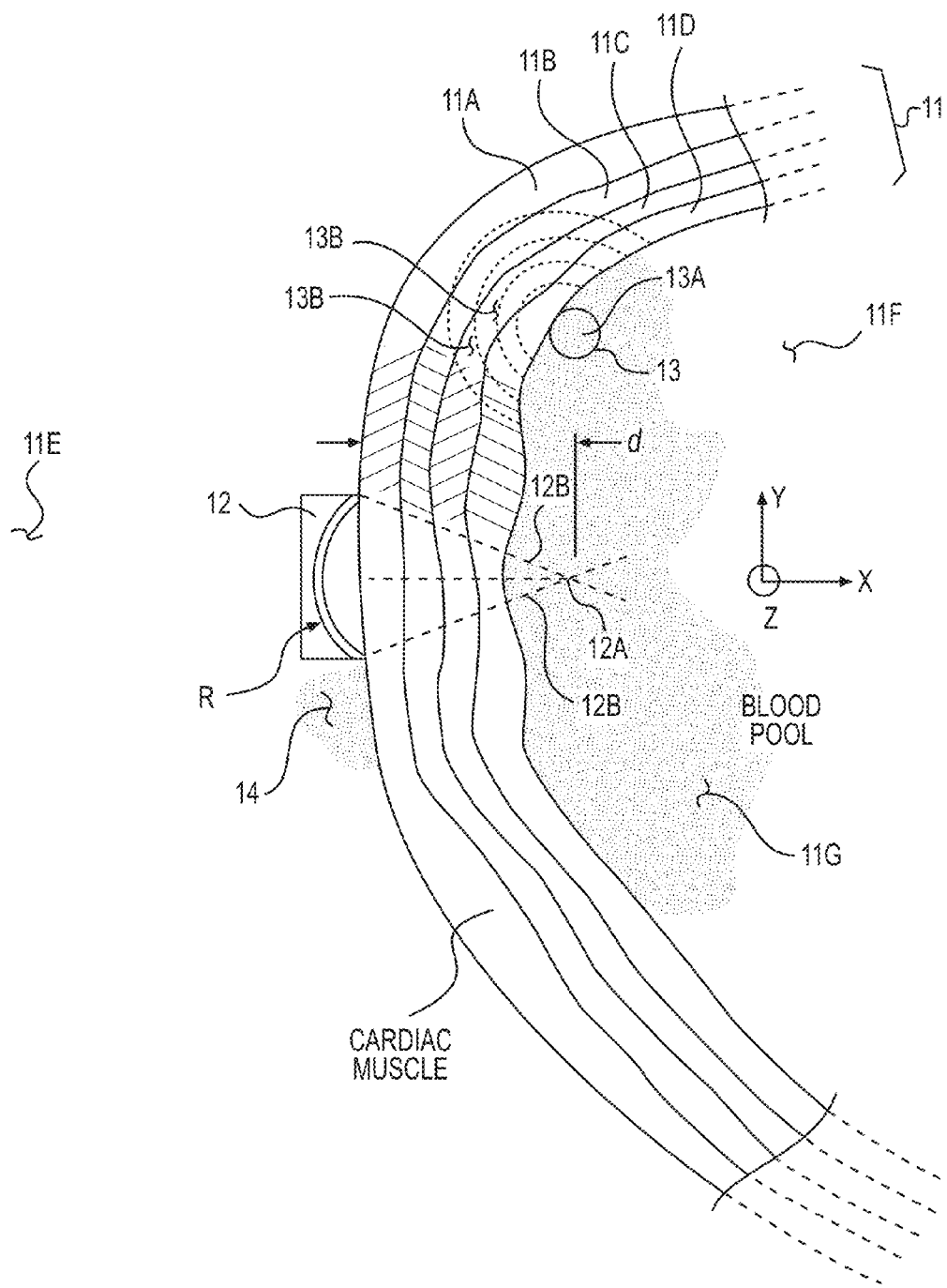
FIG. 3 is a schematic view of a layered heart wall depicting both an epicardial HIFU (High Intensity Focused Ultrasound) ablator/pinger and an endocardial RF ablator/acoustic pinger.

FIG. 3 is a schematic view of a layered heart wall depicting both an epicardial HIFU ablator/pinger and an endocardial RF ablator/acoustic pinger. FIG. 3 depicts, in sectional view, a portion of a multilayered-muscle heart wall 11. The heart wall is shown having four main layers of muscle, namely, moving inward from the heart exterior surface 11a, 11b, 11c, and 11d. Thus layer 11a is situated at the epicardium and layer 11d is situated at the endocardium. To the left of the heart and not depicted would be other bodily organs 11e such as the lung or aorta. Inside the heart is the expected heart chamber 11f with its blood pools 11g. FIG. 3 shows an epicardial HIFU ablator and acoustic pinger 12 having an acoustic beam 12b with a focal point 12a. The depth of the focal point 12a is measured from the transducer 12. As is typical the HIFU transducer 12 has a focal radius R to cause focusing at point 12a. In this example one can presume the transducer 12 is spherical in shape with a radius R. As an alternative method of ablation FIG. 3 shows an RF ablation catheter 13 in the heart chamber 1f. Typically, one or the other would be employed; however the invention applies to both types as well as to other heat-depositing ablator types such as laser and microwave ablators.

FIG. 3 shows the shape of ablated regions for each of the HIFU and RF ablators depicted. For a HIFU ablator 12 with a generally conical (spherical transducer) beam shape defined by the beam 12b and focus 12a, one typically gets a lesion which has the general shape of the beam, that lesion developing in the known manner from the initially, hottest focal region backwards toward the transducer over time. As would be expected if the HIFU transducer is operated for long periods, the lesioning action or necrosis also eventually starts to occur outside the beam-proper because of lateral thermal conduction out of the beam region. In this example, acoustic HIFU pulses are used such that the ablated necrosed lesion region approximately occurs only in the beam outline 12b or somewhat beyond that outline. HIFU pulses with interleaved cooling periods keep the tissues outside the HIFU beam relatively cool. Thus, since the HIFU transducer focus in FIG. 3 is beyond the stacked tissue layer's total thickness (11a, 11b, 11c, 11d), one expects the full tissue thickness including all of these interfaces to undergo thermal lesioning or necrosis. As is typical for an epicardial ablator such as the HIFU transducer 12, one will have some amount of liquid 14 such as saline or pericardial fluid to assure transducer cooling and excellent acoustic coupling into tissue layers 11a, 11b, 11c, 11d. The transducer 12 acts both as a HIFU ablator and a pinger in this example. Although muscle interfaces more easily and more quickly get ablated and micro-bubbled, it is important to understand that if the ablating power remains on for a longer period or higher powers are employed, then regions within the muscle layers themselves also get ablated.

The following discussion is directed to the alternative example of the depicted endocardial RF ablator/pinger 13. As is known for a typical RF ablation catheter 13 one gets a substantially hemispherical or mushroom shaped lesion depicted by growing lesion boundaries 13a, 13b and 13c. This is what is expected of what is approximately a point source of heating. The progressing RF catheter lesion fronts 13a, 13b, 13c are also depicted as including heart wall muscle layer interfaces between muscle layers 11a, 11b, 11c, 11d. Thus, for both the HIFU ablator/pinger 12 and the RF ablator/pinger 13, one can acoustically visualize the preexisting heart wall interface layers and watch them as ablation progresses to observe how micro-bubbling accumulates mainly on the interfaces. Further, one can observe the simultaneous edema or swelling of the individual and stack of muscle layers which are intercepted by the lesion outline for each ablator type. With RF ablation (versus HIFU), one is applying the greatest heat much nearer the surface (catheter tip region), so that generally the top (nearest) muscle layer and perhaps one or two muscle interfaces beneath will get necrosed depending on how thick they are relative to the given ablation power/time and irrigation.

Figure 4:
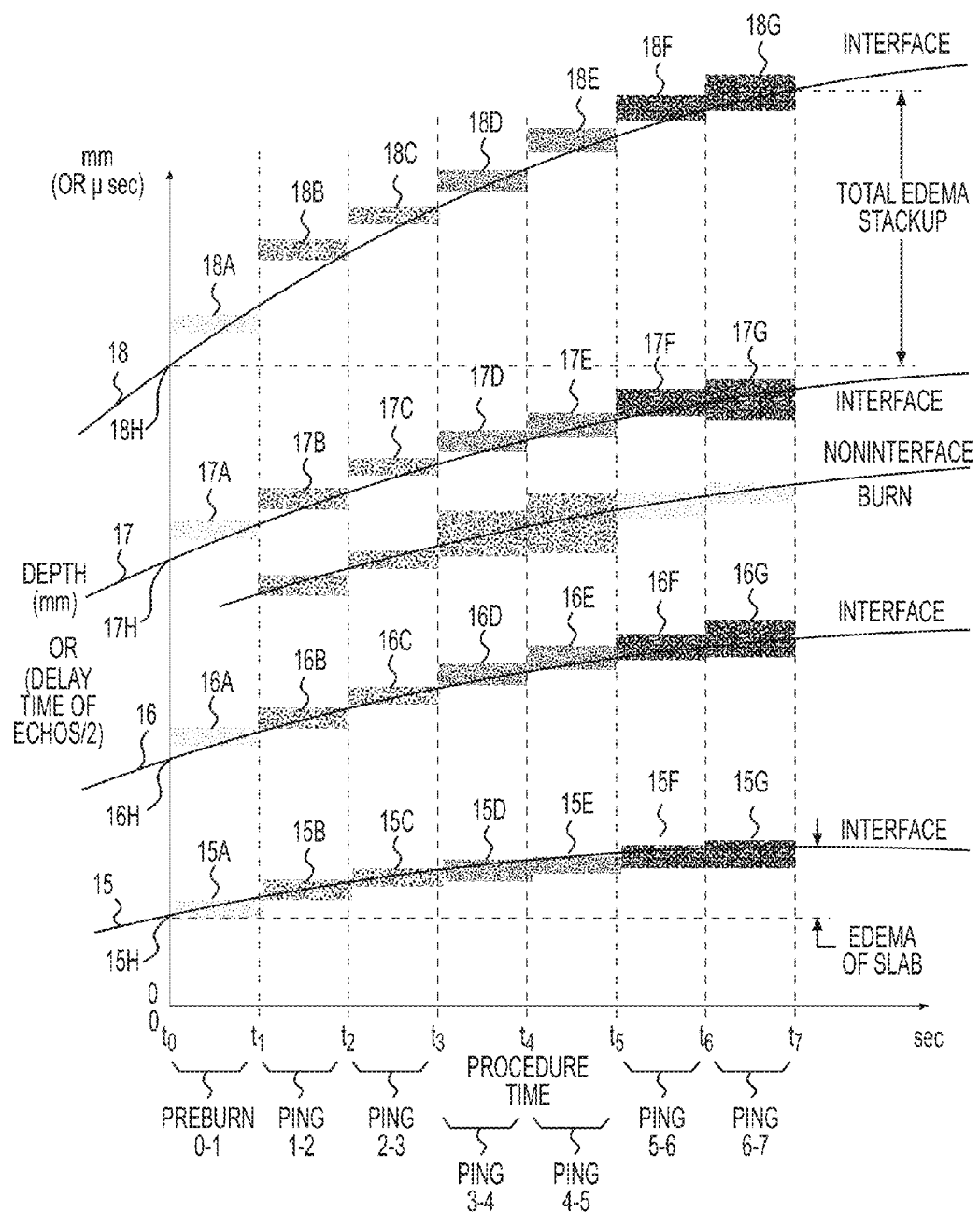
FIG. 4 is a plot of acoustic echoes received versus ablation time for the epicardial HIFU device of FIG. 3 operated in feedback pinging mode.

FIG. 4 is a plot of acoustic echoes or pings versus ablation time for the deep-heating epicardial HIFU device of FIG. 3. The plot shows, for the HIFU ablator/pinger 12, acoustic reflections from various depths before and over a period of ablation. The left vertical axis is tissue depth in mm or millimeters as conventionally determined from acoustic round-trip transit time divided by 2. The bottom horizontal axis is time into the ablation procedure measured in seconds. The main feature of the plot is growing acoustic reflections versus procedure time for the four interfaces in front of the HIFU ablator/pinger 12. Note that the fourth interface is the tissue/blood endocardial interface. Immediately it can be seen that the depths of the four interfaces increase over time as edema thickens the individual layers and their total summed thickness. The strength of acoustic reflection is depicted as a black dot density. In other words, the blacker the overall dot density, the stronger is the acoustic reflection. The main thing to notice is that for the various interfaces the acoustic reflectivity increases from left to right as micro-bubbles accumulate with increasing ablation time. At the same time, these interfaces move further and further away from the transducer 12 due to swelling edema's increasing their depths. Note at the upper right hand side of FIG. 4 that the accumulated edema from all the layers is summed if the transducer is held at zero depth.

A number of observations can be made regarding the plot in FIG. 4 which is specifically for the deep-heating HIFU transducer/pinger 12. Because the ablator is a transducer 12, it is easily operated in both ablative CW modes (such as pulsed CW) and in pulsed pinging mode in an interleaved manner. In the plot of FIG. 4, there are eight time points t0 through t7 on the horizontal procedure time axis. They are as follows:

Period from t0 to t1—Before any ablation-taking of background reflection data
Period from t1 to t2—Sampling of 20 sequential reflection spectra after 1st subburn
Period from t2 to t3—Sampling of 20 sequential reflection spectra after 2nd subburn
Period from t3 to t4—Sampling of 20 sequential reflection spectra after 3rd subburn
Period from t4 to t5—Sampling of 20 sequential reflection spectra after 4th subburn
Period from t5 to t6—Sampling of 20 sequential reflection spectra after 5th subburn
Period from t6 to t7—Sampling of 20 sequential reflection spectra after 6th subburn Individual equivalent ablative subburns occur at t1 through t6 points; however, this plot does not show the subburn durations themselves. The plot only shows the subburn following 20 sequential pinged reflection data. This is by convention because one preferably does not burn and ping at the same time as this causes a severe electrical noise problem. As an example, the inventors subburn for 6 seconds and then plot the 20 reflection scans after that subburn is delivered over a pinging 10 second period. Again the plot shows only the pinging time extent and not the ablating time extent.

In the plot of FIG. 4 for the deep-heating HIFU probe 12, one sees the following interfaces:
Interface 15 which is the interface between FIG. 3 layers 11a/11b
Interface 16 which is the interface between FIG. 3 layers 11b/11c
Interface 17 which is the interface between FIG. 3 layers 11c/11d
Interface 18 which is the interface between FIG. 3 layer 11d and the blood pool 11g Note that the preburn initial depth locations of these interfaces are at points 15h, 16h, 17h and 18h on the vertical axis of FIG. 4. Note again that the depths of the interfaces increase from left to right as edema swell the layers and as ablation micro-bubbles and thermal damage accumulate. For each interface such as interface 16, FIG. 4 labels the preburn period 16a and the postburn periods 16b-16g. Interface 15 has preburn period 15a and postburn periods 15b-15q. Interface 17 has preburn period 17a and postburn periods 17b-17q. Interface 18 has preburn period 18a and postburn periods 18b-18g.

The amplitude of a reflection for a particular depth or interface depends on the absolute reflectivity of the interface or tissue at the depth and the intervening cumulative attenuation between the transducer and that interface or depth. If one has a very highly reflective near-transducer interface for a given period, then that high reflectivity effectively attenuates the amount of acoustic energy that can proceed more deeply for that period. The effect of this is that near reflectors suppress deeper reflectors from being detected. However, the inventors have found that over the period of a lesioning process, this "masking" effect varies as bubble clouds come and go such that one can typically see strong reflections (well above the noise level) during at least part of the total ablation cycle for all ablated depths and interfaces. The inventors have found that any new incremental reflectivity seen at depth is an indication of ablation damage underway at that depth. By "new" we mean incremental or new reflectivity relative to what was at that depth before ablation. Note that one might see new reflectivity which "goes away" due to later microbubble clouding and masking near the surface. The fact is the ablation damage does not go away; it just attenuatively becomes masked. Thus, one should look for reflectivity increases anywhere during the ablation procedure at all depths.

The following discusses useful algorithms for monitoring ablation. First, as stated, any increase in reflectivity at a given depth over preexisting reflectivity at that depth indicates ablative damage is proceeding at that depth regardless of whether that reflective increase takes place at a muscle interface or not. Time should be allowed for the damage to accumulate at that depth and in adjacent (deeper and shallower) nearby tissues. Second, muscle interfaces, if they fall within a lesion zone, can be employed to track edema. Increased reflectivity at such a muscle interface indicates ablative damage is underway at the interface. Time should be allowed for damage to accumulate at the interface and at depths above and below the interface understanding that interfaces are the first to show damage if in-range of the ablation heat source.

The inventors have found a peak-hold strategy useful wherein for each pinged depth one retains in computer memory the maximum reflectivity increase (if any) seen at any time point during or after the ablative process. This approach nicely takes into account the above acoustic masking phenomenon.

From the above description, it can be seen that there are several features to look for regarding lesioning progress and these are:

1) all increases in reflectivity at any depth in any tissue relative to original nonablated reflectivity, even if apparently temporary;

2) increases in reflectivity appearing, at least temporarily, at muscle interfaces, 3) for RF catheter lesions in particular, the reflectivities before and after RF power is stopped for each interleaved ping measurement (this quickly dissipates the considerable RF nearfield micro-bubble cloud and thereby accentuates the unchanging crosslinking and necrosis related damage); and 4) to a lesser but finite degree, the total amount of edema swelling along the lesion depth, most easily tracked by watching muscle interface translation due to the edema.

The inventors have found that features 1-4 correlate with actual lesion depths as determined histologically. What this means is that if one sees increasing micro-bubble reflectivity at a given depth, it can be safely assumed, during that period, that the tissue depth is experiencing temperatures likely in the 65-100 Deg C. range. Such temperatures are easily high enough that cells are killed in a few seconds at that temperature if power is maintained.

The ablation and pulse-echo monitoring can be performed using the apparatus of FIGS. 1 and 2, or other suitable devices. The control unit 130 is configured to control the ablation element and the acoustic pinger transducer so as to, prior to thermal ablation of the tissue, direct an acoustic pulse-echo beam to the tissue to obtain pre-ablation acoustic reflections from the tissue, and during thermal ablation of the tissue, direct an acoustic pulse-echo beam to the ablated tissue to obtain acoustic reflections from the ablated tissue for acoustic pulse-echo feedback. The analyzer 132 is configured to compare the acoustic reflections from the ablated unlayered or layered tissue with the pre-ablation acoustic reflections to assess the ablative progress of the target tissue. The ablative progress can be assessed by monitoring one or more of the four features described above.

Figure 5:
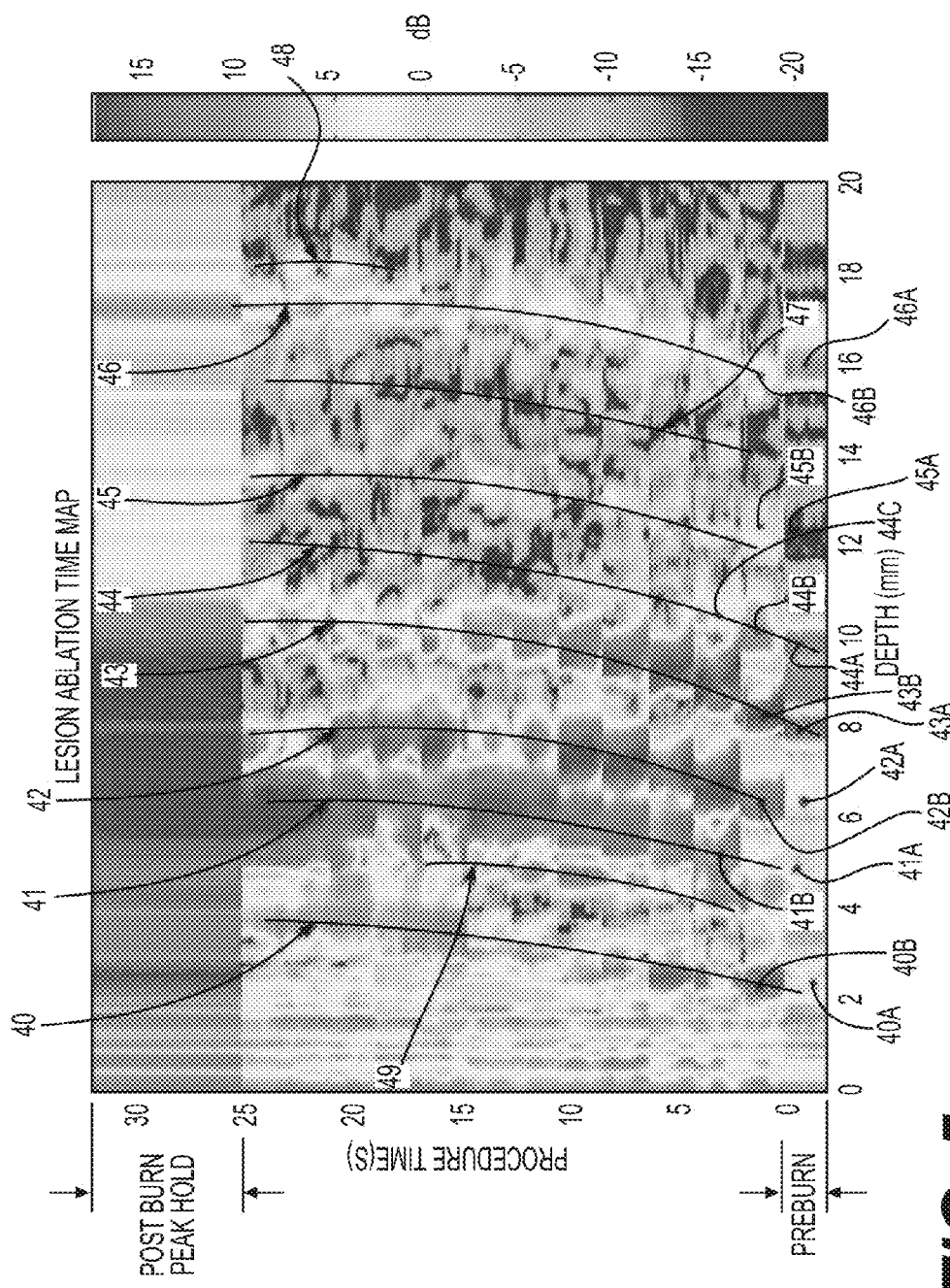
FIG. 5 is an actual experimental data plot from living thigh muscle done along the lines of FIG. 4.

FIG. 5 is an actual deep-burning HIFU ablator experimental data plot from living thigh muscle done along the lines of FIG. 4. The actual plot is an approximately 40 dB (logarithmic) color scale of reflective acoustic amplitude for pig thigh muscle (shown here in black and white). The actual plot is shown here in black and white without loss of illustrative details since it is similar to the schematic illustration of FIG. 4. The procedure time (as in FIG. 4) is along the first axis and the tissue-depth is along the second axis. The top of the color scale (reds) are very strong reflectors whereas at the bottom of the scale (blues) there are weak or undetectable reflection amplitudes. The middle of the scale is yellow. Looking along the procedure time axis, there is again a preburn reflection assessment period (the time before 0), and after time 0 there are about 12 time segments; in each time segment there are about 20 depth scans over about 10 seconds. The burning time (not shown) occurs before each of the 12 sampling times. Arc 40 is mostly red (40b) and yellow. Arc 41 turns from blue at 41a to yellow and then red at 41b and beyond. Arc 42 is mostly red (42b) with some yellow. Arc 43 is mostly red (43b) with some yellow and blue. Arc 44 turns from red at 44a and 44b to yellow at 44c and then mostly blue. Arc 45 is mostly blue with some yellow. Arc 46 is mostly yellow (46b) with some red and blue. Arc 47 is mostly blue. Arc 48 has blue and yellow. The first thing to notice is that several preburn detectable tissue interfaces are visible in the preburn reflection period. Specifically, one sees preexisting interfaces such as, for example, 40a, 42a, 43a, 44a, and 46a. Second, some of these interfaces are burned over time (become more reflective) such as 40, 49, 43, and 44. At the same time they progress deeper into the tissue over time due to edema swelling. Third, there are cases where an initial reflective interface which burns for a period and then disappears (due to masking), such as 44a, 44b, 44c (red turning to yellow turning to blue). Fourth, the plot shows some burning (increased reflectivity) suddenly appear at depths not apparently associated with preexisting interfaces such as 45a (generally blue) and 45b (yellow suddenly appearing at some depths). Note that these edema-deepened colored arcs or curves appear for any reflective site in the tissue, regardless of whether it is a burning preexisting interface or a new burn site which appears off such a preexisting interface. As would be mechanically expected, one observes that relative to the transducer/tissue surface ("0" depth), the curvature of the colorized arcs increases with depth simply because all the swelling layers form a swelling sandwich. Moreover, looking at arc 41, one sees the amount and degree of burning increasing with time (i.e., as seen along the arc) (blue turning to yellow turning to red). Arc 41, again, is a burn region which appears away from a preexisting interface. In general the edema accumulates over a period of minutes as ablative exposure continues. Roughly speaking the total amount of edema (feature #4) correlates with the lesion depth; however, the best and relatively immediate indicators of ablative damage are features #1-3 above.

It should be emphasized that the degree of color or redness (ablation degree) in these plots depends on two factors, namely, the absolute reflectivity of the tissue location at that depth, and masking or attenuation caused by shallower burning because burned tissue is also more attenuative than unburned tissue. A good example of the masking phenomenon is provided by arc 44 of FIG. 5 along which reflectivity is dramatically reduced with time because the three or so shallower interfaces above it become burned (more attenuating).

The following describes the mechanisms for causing increasing redness (ablative necrosis) in FIG. 5. The inventors believe the predominant mechanisms are desiccation (crosslinking) and micro-bubble formation. The micro-bubbles form most easily, from an energy perspective, in preexisting wetted interfaces but they can also form in bulk tissue. Micro-bubbles can form within tissue away from interfaces; however, it takes somewhat more heat so that this generally happens after some initial interface burning. Thus one sees most increases in reflectivity happen in interfaces plus some additional increases or appearances away from interfaces. Increases in interfaces relative to the preburn state can only be caused by that interface being itself more reflective in an absolute sense. When tissue proteins crosslink, the micro-bubbles can be stabilized for very long periods. This is akin to frying an egg and observing stable bubbles "cooked into" in the solidified white-portion of the egg. Micro-bubbles in bench (non-living) tissues last the longest because of the complete lack of perfusion. Although cross-linked protein in necrosed tissue is somewhat harder and higher velocity than unburned tissue, it does not show up in B-Mode ultrasound imaging as is known. However, it can be seen in the substantially more complex elastographic (stiffness) imaging modality.

It is the inventors' experimental bench and clinical-animal experience that for lesioning processes utilizing applied RF or CW HIFU power over tens of seconds, if one sees changing or new reflectivity (greater than a 5 dB increase) at a particular depth, then the lesion is at least that deep and is contiguous above that depth after just a few seconds unless surface irrigation is applied. This makes sense because such prolonged ablations provide ample time for lateral diffusion of heat and for that heat to ablate tissue. As an example of this, the plot of FIG. 5 shows new reflective contrast (more red) along arcs 45 and 47 and 48 as well as increase contrast late on arc 46 (yellow). Indeed, this burn was about 18 mm deep upon sectioning.

FIG. 5 shows that not only does the color get redder and redder with ablation but the reddened areas also increase in area. A redder color at a point in tissue (relative to preburn) means its more burned while a larger or growing area of redness means that the ablated region is growing or spreading physically.

Based on the features described above involving pulse-echo (pinging) monitoring and control of thermally ablative lesioning in unlayered or layered tissues, an aspect of the invention is directed to a system for thermally ablating a target tissue and monitoring the ablative progress utilizing acoustic pulse-echo feedback. The system includes an ablation device which is capable of ablating a tissue region utilizing an ablative energy; an acoustic pulse-echo transducer which is capable of acoustically pinging the above tissue; and powering, control sources, cabling and necessary user interfaces to power and control the ablative energy device and the pinging transducer. The ablation device and the pinger transducer are capable of being coupled to the target tissue such that ablative lesion-forming energy can be deposited in the tissue by the ablation device and pinging acoustic pulses and their associated reflections from lesioning-associated reflectors can be respectively passed into and from the tissue. The system can be used to assess a preburn initial state of acoustic reflections and thereafter to assess changes in reflectivity with ablation. The reflectivity changes focus on increases above what was present preablation, said increases possibly being only temporarily visible due to later overlying masking effects; thus the reflectivity peak-hold strategy to record the reflective maxima versus depth which we find correlates with actual lesion histology.

The ablation device may be any of a HIFU transducer, a monopolar or bipolar RF electrode, a laser, or a microwave tip. The pinging transducer may be any of a magnetostrictive, piezoceramic, piezopolymer, MEMS or CMUT, electrostatic, or piezocomposite transducer. The pinged depth-range should include the entire intended ablation depth range plus some safety factor. The pinger may alternatively be moved or scanned relative to an ablatable region. The ablation device may be a HIFU transducer and the pinging may also be done using the HIFU transducer. The pinging transducer may be mechanically focused. An aspect of ablation is determined or controlled using at least some pinged feedback. The pinged feedback is provided to a practitioner in the form of a quantitative or qualitative guide to the extent of lesioning attained. This is based on the above-mentioned peak-hold approach or recording of the maximum reflectivity seen at each depth at any time during the ablation or thereafter. The ablation device and pinger elements may be held or fixed to a tissue position while ablation and pinging are carried out. The holding may be achieved by vacuum clamping. A monitored amount of edema swelling displacement may also be considered in determining at least whether ablation took place and/or possibly also the extent of ablation. A disadvantage of edema phenomenon is that edema is not immediate and is cumulative over minutes, so that the first three features are the most useful for "realtime" feedback. The ablation and pinging devices may be contained in or on a catheter, a catheter tip, a scope, or a manipulatable handheld or robot-held wand or articulator.

Another aspect of the invention is directed to a system for thermally ablating an unlayered or layered target tissue and monitoring the ablative progress utilizing acoustic pulse-echo feedback. The system includes an ablation device which is capable of ablating a tissue region; an acoustic pulse-echo transducer which is capable of pinging the above tissue; and powering, control sources, cabling and necessary user interfaces to power and control the ablative energy device and the pinging transducer. The ablation device and the pinger transducer can be coupled to the target tissue such that ablative lesion-forming energy can be deposited in the tissue and pinging acoustic pulses and their associated reflections from acoustic reflectors can be respectively passed to and from the tissue. In the case of an RF pinger, fewer layered muscle interfaces are typically within an ablation zone as compared to typically deeper HIFU lesions. The system is used to assess a preburn initial state of acoustic reflections caused by pre-existing bulk tissue structure and/or interfaces between any layers that may be in-range and may also be capable of tracking the amount of edema swelling as indicated by the deepening interfaces.

In a preferred embodiment, the ablation and pinging are interleaved in time. The ablation and pinging may alternatively occur simultaneously, but it is generally not desirable due to electrical noise from the ablator entering the pinger receiver. A more desirable approach is to have sequential and periodic ablation and pinging with high duty cycle ablation (e.g., more than about 60%, preferably more than about 90%, and more preferably about 99%) and low duty cycle pinging (e.g., less than 40%, preferably less than about 10%, and more preferably about 1%). The low duty cycle pinging ensures that it does not materially affect the heating rate needed to achieve the desired ablation by unduly reducing the ablation time. The pinging may utilize a frequency in the range of about 1 MHz to about 25 MHz, preferably about 5-15 MHz, and more preferably about 6-10 MHz. A pre-ablation pinging records the initial baseline values of reflectivity versus depth. One may optionally choose, as part of the algorithm, to normalize to 1 or unity the starting reflectivities such that different lesions can be compared in terms of percentage change in reflectivities, for example. The system either provides feedback to the practitioner or the system has its own internal feedback loop such that in either case sensed reflections are available to modify, modulate, or gate ablation delivery. The pinging capability may also provide warning or indication of tissue popping or incipient popping. Warning inaudible pre-pops comprise short term appearances of nearfield (particularly for surface irrigated RF) masking bubble clouds which usually dissipate after a few seconds, until a later occurrence wherein they audibly explode instead. Thus, algorithm wise, if one looks for sudden masking of deep reflectivities one will note these prepop events and possibly reduce power in response to avoid a damaging audible pop. The pinging capability may further provide information as to the depth of an anatomical feature or of a tissue thickness. Finally, the operation of the pinger transducer in pulsed (or even CW continuous wave) mode also allows the user, as described, to deduce what the force-load is on the catheter tip. A given ping event may provide information regarding one or more of lesion status, prepop status, or tip force.

The inventors note that the inventive ablator device might have two or even more acoustic transducers, such as a first for forward-directed lesion making and a second for side-directed lesion making. For a conventional RF tip ablator this would conveniently allow individually optimized monitoring of tip-made lesions and sidewall made lesions. A side-looking transducer may need to be rotated toward the tissue by the user.

In the description, numerous details are set forth for purposes of explanation in order to provide a thorough understanding of the present invention. However, it will be apparent to one skilled in the art that not all of these specific details are required in order to practice the present invention. Additionally, while specific embodiments have been illustrated and described in this specification, those of ordinary skill in the art appreciate that any arrangement that is calculated to achieve the same purpose may be substituted for the specific embodiments disclosed. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. An ablation catheter with acoustic monitoring, the ablation catheter comprising:
    an elongated catheter body extending longitudinally between a proximal end and a distal end along a longitudinal axis;
    a distal member disposed adjacent the distal end, the distal member including an ablation element to ablate a biological member at a target region outside the catheter body; and
    one or more acoustic transducers each configured to direct an acoustic beam toward a respective target ablation region and receive reflection echoes therefrom;
    wherein the distal member includes a transducer housing in which the one or more acoustic transducers are disposed, the transducer housing including at least one transducer window through which the acoustic beam passes, the at least one transducer window portion of the distal member being at least 50% carbon by volume, the at least one transducer window being thermally and electrically conductive and having an acoustic impedance between an acoustic impedance of the one or more acoustic transducers and an acoustic impedance of the biological member;
    wherein the distal member is thermally and electrically conductive and is at least 50% carbon by volume.

2. The ablation catheter of claim 1,
    wherein the at least one transducer window is at least about 90% carbon by volume.

3. The ablation catheter of claim 2,
    wherein the at least one transducer window is about 100% carbon by volume.

4. The ablation catheter of claim 1,
    wherein the at least one transducer window comprises a carbon matrix material which is exterior surface-infused with a noble metal.

5. The ablation catheter of claim 1,
    wherein the at least one transducer window includes an exterior surface-infused or overlying coating of noble metal.

6. The ablation catheter of claim 1,
    wherein the at least one transducer window spans 360 degrees around the one or more acoustic transducers.

7. The ablation catheter of claim 1,
    wherein the distal member comprises a carbon matrix material which is exterior surface-infused with a noble metal.

8. The ablation catheter of claim 1,
    wherein the distal member is made substantially entirely of carbon.

9. The ablation catheter of claim 8,
    wherein the distal member comprises a surface coating of noble metal on an exterior surface thereof, and the distal member is more than about 90% by volume carbon.

10. The ablation catheter of claim 1,
    wherein the at least one transducer window has an acoustic impedance of about 20-30 mega Rayles (kg/m2s).

11. The ablation catheter of claim 1,
    wherein the at least one transducer window comprises an acoustic lens having a concave external surface.

12. An ablation apparatus having the ablation catheter of claim 1, further comprising:
    a control unit configured to control the ablation element and the one or more acoustic transducers so that thermal ablation of the biological member and passage of the acoustic beam to and from the biological member occur sequentially and periodically.

13. The ablation apparatus of claim 12,
    wherein the control unit is configured to control the ablation element and the one or more acoustic transducers so that the thermal ablation of the biological member has a high duty cycle of more than about 90% and the directing of the acoustic beam passage to and from the biological member has a low duty cycle of less than about 10%.

14. The ablation catheter of claim 1,
    wherein the one or more acoustic transducers include a sideways-directed acoustic transducer oriented in a sideways direction non-parallel to the longitudinal axis to monitor a sideways-formed lesion and a forward-directed acoustic transducer oriented in a forward distal direction parallel to the longitudinal axis to monitor a forward-facing lesion, respectively.

15. The ablation catheter of claim 14,
    wherein the distal member is rotatable to direct acoustic beam from the sideways-directed acoustic transducer through the at least one transducer window toward a target tissue on a side of the distal member.

16. The ablation catheter of claim 1,
    wherein a remaining portion of the distal member, other than the at least one transducer window portion, comprises one or more materials selected from the group consisting of metal, ceramic, cermet, and glass.

17. An ablation catheter with acoustic monitoring, the ablation catheter comprising:
    an elongated catheter body extending longitudinally between a proximal end and a distal end along a longitudinal axis;
    a distal member disposed adjacent the distal end, the distal member including an ablation element to ablate a biological member at a target region outside the catheter body; and
    one or more acoustic transducers each configured to direct an acoustic beam toward a respective target ablation region and receive reflection echoes therefrom
    wherein the distal member includes a transducer housing in which the one or more acoustic transducers are disposed, the distal member being at least 50% carbon by volume, the distal member being thermally and electrically conductive and having an acoustic impedance between an acoustic impedance of the one or more acoustic transducers and an acoustic impedance of the biological member.

18. The ablation catheter of claim 17,
wherein the distal member is at least about 90% carbon by volume.

19. The ablation catheter of claim 17,
wherein the distal member is about 100% carbon by volume.

20. The ablation catheter of claim 17,
wherein the distal member has a surface-infused or overlying coating of noble metal on an exterior surface thereof.

21. The ablation catheter of claim 17,
wherein the distal member has an acoustic impedance of about 20-30 mega Rayles (kg/m2s).

22. An acoustic monitoring method for an ablation procedure using an ablation catheter which includes an elongated catheter body extending longitudinally between a proximal end and a distal end along a longitudinal axis; a distal member disposed adjacent the distal end, the distal member including an ablation element to ablate a biological member at a target region outside the catheter body; and at least one acoustic transducer, the distal member including a transducer housing in which the at least one acoustic transducer is disposed, the transducer housing including at least one transducer acoustic window each corresponding to the respective at least one acoustic transducer and through which respective acoustic beam from the respective at least one acoustic transducer passes, the at least one transducer window being at least 50% carbon by volume, the at least one transducer window being thermally and electrically conductive and having an acoustic impedance between an acoustic impedance of the at least one acoustic transducer and an acoustic impedance of the biological member, the distal member being thermally and electrically conductive and at least 50% carbon by volume; the method comprising:
thermally ablating the biological member at the target region with the ablation element; and
directing an acoustic beam through the acoustic window to and from the biological member.

23. The acoustic monitoring method of claim 22,
wherein directing the acoustic beam to and from the biological member comprises at least one of acoustic lesion feedback of the biological member being ablated, a tissue thickness measurement in a region of the biological member being ablated, a tissue proximity measurement in a region of the biological member being ablated, a pre-pop warning of the biological member being ablated, a pre-pop detection of the biological member being ablated, or sensing of a tissue contact force on the distal member.

24. The acoustic monitoring method of claim 22,
wherein the thermally ablating the biological member and the directing the acoustic beam to and from the biological member occur sequentially and periodically.

25. The acoustic monitoring method of claim 24,
wherein the thermally ablating of the biological member has a high duty cycle of more than about 90% and the directing of the acoustic beam to and from the biological member has a low duty cycle of less than about 10%.

* * * * *